(12) United States Patent
Nomura

(10) Patent No.: US 8,911,359 B2
(45) Date of Patent: Dec. 16, 2014

(54) GUIDE SHEATH AND MEDICAL SYSTEM

(71) Applicant: Olympus Medical Systems Corp., Tokyo (JP)

(72) Inventor: Yusuke Nomura, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/043,987

(22) Filed: Oct. 2, 2013

(65) Prior Publication Data

US 2014/0094658 A1 Apr. 3, 2014

Related U.S. Application Data

(63) Continuation of application No. PCT/JP2013/053809, filed on Feb. 18, 2013.

(60) Provisional application No. 61/608,280, filed on Mar. 8, 2012.

(51) Int. Cl.

| A61B 1/04 | (2006.01) |
|---|---|
| A61B 1/00 | (2006.01) |
| A61B 1/018 | (2006.01) |
| A61B 17/29 | (2006.01) |
| A61B 17/00 | (2006.01) |
| A61B 10/02 | (2006.01) |
| A61B 17/34 | (2006.01) |

(52) U.S. Cl.
CPC ......... *A61B 1/00154* (2013.01); *A61B 1/00098* (2013.01); *A61B 1/018* (2013.01); *A61B 1/00133* (2013.01); *A61B 2017/2905* (2013.01); *A61B 2017/003* (2013.01); *A61B 2017/00296* (2013.01); *A61B 2017/00305* (2013.01); *A61B 2017/0034* (2013.01); *A61B 2017/00809* (2013.01); *A61B 1/00078* (2013.01); *A61B 2010/0216* (2013.01); *A61B 2017/00309* (2013.01); *A61B 2017/345* (2013.01)
USPC .............................. 600/114; 600/140; 600/146

(58) Field of Classification Search
CPC ........... A61B 1/00154; A61B 1/00078; A61B 1/00098; A61B 2017/003; A61B 2017/2905
USPC .......................................... 600/114, 140, 146
See application file for complete search history.

(56) References Cited

U.S. PATENT DOCUMENTS

| 5,921,915 | A | * | 7/1999 | Aznoian et al. | 600/104 |
|---|---|---|---|---|---|
| 2011/0196204 | A1 | * | 8/2011 | Setty et al. | 600/120 |
| 2012/0071722 | A1 | * | 3/2012 | Nakamura et al. | 600/140 |
| 2012/0165680 | A1 | * | 6/2012 | Akifumi | 600/466 |
| 2012/0184817 | A1 | * | 7/2012 | Sugiyama | 600/114 |
| 2012/0190988 | A1 | * | 7/2012 | Harhen | 600/466 |
| 2013/0178703 | A1 | * | 7/2013 | Konstorum | 600/114 |

FOREIGN PATENT DOCUMENTS

| JP | 58-108801 A | 7/1983 |
|---|---|---|
| JP | 61-171902 A | 10/1986 |

(Continued)

OTHER PUBLICATIONS

International Search Report dated May 7, 2013 issued in PCT/JP2013/053809.

*Primary Examiner* — Nicholas Lucchesi
*Assistant Examiner* — Gerald Landry, II
(74) *Attorney, Agent, or Firm* — Scully, Scott, Murphy & Presser, P.C.

(57) ABSTRACT

A guide sheath includes: an elongated member extending along a longitudinal axis; a manipulation wire extending along the longitudinal axis of the elongated member so as to be capable of advancing and retracting; a bent section formed of a thermoplastic resin in a tubular shape and configured to be bent in accordance with advance or retraction of the manipulation wire; and a first hard section provided at a distal end surface of the bent section and formed by cross-linking the thermoplastic resin to which a distal end section of the manipulation wire is fixed.

2 Claims, 11 Drawing Sheets

(56) References Cited

FOREIGN PATENT DOCUMENTS

| | | |
|---|---|---|
| JP | 2-10802 A | 1/1990 |
| JP | 03-280918 A | 12/1991 |
| JP | 08-057035 A | 3/1996 |
| JP | 2005-287963 A | 10/2005 |
| JP | 2007-289467 A | 11/2007 |
| JP | 4624483 B | 2/2011 |
| WO | WO 2012/005124 A1 | 1/2012 |

* cited by examiner

GUIDE SHEATH AND MEDICAL SYSTEM

This application is a continuation application based on a PCT Patent Application No. PCT/JP2013/053809, filed Feb. 18, 2013, whose priority is claimed on U.S. Provisional Patent Application No. 61/608,280, filed Mar. 8, 2012. The contents of both the PCT Application and the US Application are incorporated herein by reference.

BACKGROUND OF THE INVENTION

1. Field of the Invention

The present invention relates to a guide sheath used under guidance of an internal introduction device, and a medical system including the guide sheath.

2. Description of Related Art

In the related art, a catheter tube configured to be inserted into a body cavity, a blood vessel, or the like, and inject liquid medicine or discharge body fluid is used. Such a catheter tube is disclosed in, for example, Japanese Unexamined Patent Application, First Publication No. H08-57035. The catheter tube is formed by continuously varying degrees of cross-linking of a synthetic resin in a longitudinal direction.

In manufacturing the catheter tube, a synthetic resin sensitive to cross-linking treatment by radiation or the like and a synthetic resin insensitive thereto are combined. Then, a tube melted and extruded while continuously varying a mixing ratio of these synthetic resins is cross-linked using radiation of a β ray or the like. As the catheter tube is configured as described above, damage to organs can be prevented by a soft distal portion of the catheter tube while maintaining torque controllability and pushability by a hard proximal portion thereof.

In a treatment tool for an endoscope (hereinafter, simply referred to as a "treatment tool") disclosed in Japanese Patent No. 4624483, a cross-linked section is formed by performing cross-linking treatment on a sheath formed of a thermoplastic resin. The cross-linked section generally has good heat resistance and physical strength. For this reason, for example, when a treatment unit heated to a high temperature by a high frequency current comes in contact with a sheath or when the treatment unit compresses the sheath upon pulling the treatment unit thereinto, melting or deformation of the sheath can be prevented.

Meanwhile, when the treatment tool is inserted into an introduction channel formed in the endoscope (an internal introduction device) and used, a distal end of a guide sheath is fixed while protruding from a distal end of the introduction channel to a predetermined position, and the treatment tool is inserted into the guide sheath. According to the above-mentioned procedure, the distal end of the treatment tool can be easily positioned when the treatment tool is changed from the introduction channel.

SUMMARY OF THE INVENTION

According to a first aspect of the present invention, a guide sheath, which is configured to be guided by an internal introduction device and be inserted into a body, and which has a channel through which a medical device is capable of being inserted so as to guide a distal end of the medical device to a target area, includes: an elongated member extending along a longitudinal axis; a manipulation wire extending along the longitudinal axis of the elongated member so as to be capable of advancing and retracting; a bent section formed of a thermoplastic resin in a tubular shape and configured to protrude from a distal end of the internal introduction device and be bent in accordance with advance or retraction of the manipulation wire; and a first hard section provided at a distal end surface of the bent section and formed by cross-linking the thermoplastic resin to which a distal end section of the manipulation wire is fixed.

According to a second aspect of the present invention, in the guide sheath according to the first aspect, a conduit line may be formed at the bent section along the longitudinal axis of the elongated member, and may be disposed to be deviated with respect to a central axis of the elongated member outward in a radial direction of the elongated member. The manipulation wire may be disposed in the conduit line. The first hard section may include a partition wall between an outer circumferential surface of the bent section and the conduit line.

According to a third aspect of the present invention, the guide sheath according to the second aspect may further include: a soft section having bending stiffness smaller than that of the first hard section; and a plurality of second hard sections having the same bending stiffness as the first hard section and formed by cross-linking the thermoplastic resin. The bent section may be configured by disposing the first hard section and the plurality of second hard sections on the soft section in a direction along the longitudinal axis at intervals.

According to a fourth aspect of the present invention, in the guide sheath according to the third aspect, the soft section may have the thermoplastic resin.

According to a fifth aspect of the present invention, in the guide sheath according to the fourth aspect, the soft section may be formed of a kneading material in which the thermoplastic resin and a cross-linking accelerator are kneaded. The first hard section and the plurality of second hard sections may be formed of a cross-linked material obtained by radiating ionizing radiation to the kneading material to cross-link the thermoplastic resin.

DETAILED DESCRIPTION OF THE INVENTION

First Embodiment

Hereinafter, a first embodiment of a medical system according to the present invention is described with reference to FIGS. 1 to 8. In the following embodiment, an example in which an internal introduction device is an endoscope and a medical system is an endoscope system is described.

Figure 1:
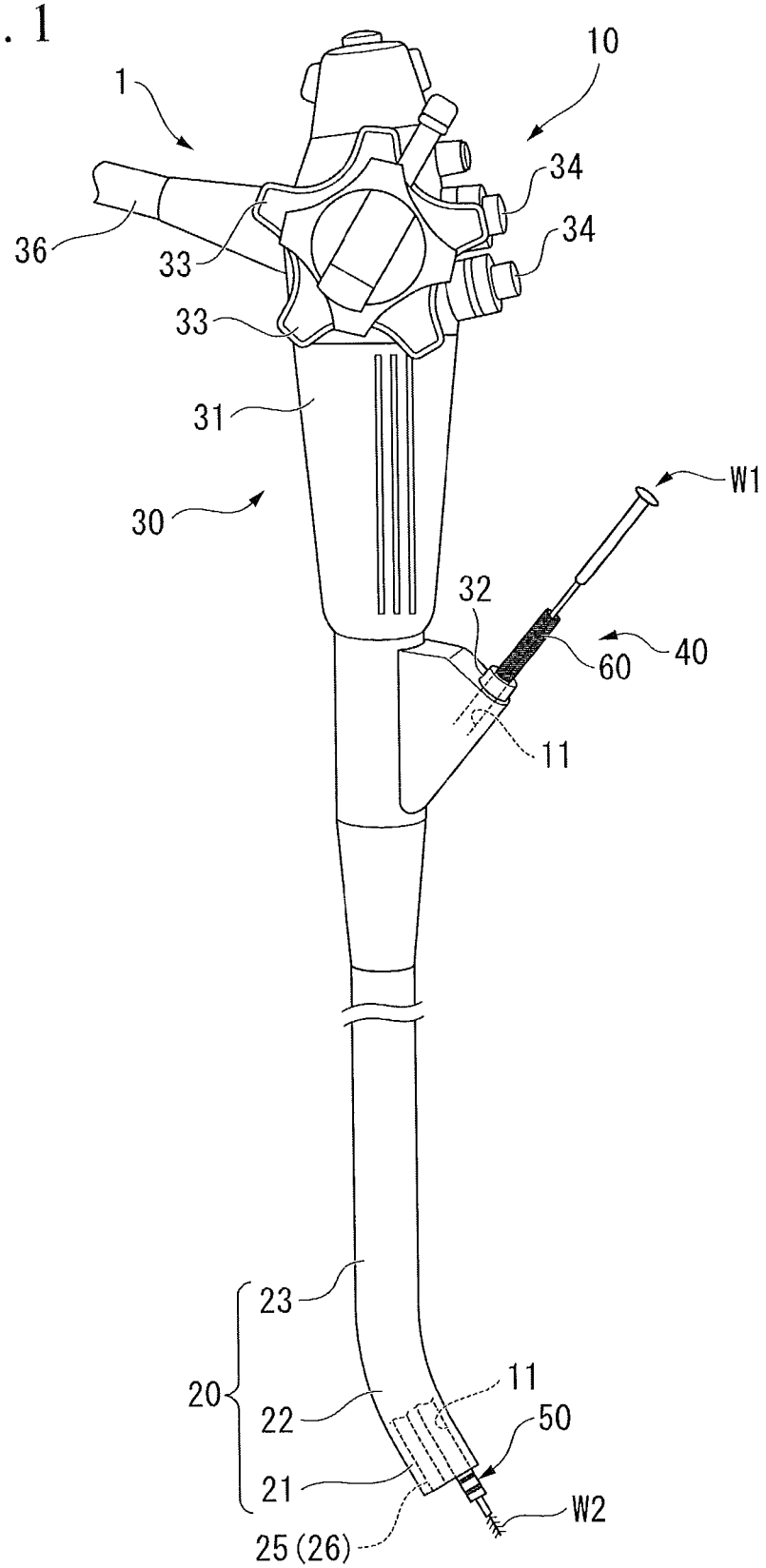
FIG. 1 is an overall view of an endoscope system according to a first embodiment of the present invention.

As shown in FIG. 1, an endoscope system 1 of the embodiment includes an endoscope 10 and a guide sheath (an elongated member) 40. An introduction channel 11 is formed in the endoscope 10. The guide sheath 40 can be inserted into the introduction channel 11.

The endoscope 10 includes a long insertion unit 20 and a manipulation unit 30. The manipulation unit 30 is provided at a proximal end of the insertion unit 20. The insertion unit 20 has a distal end hard section 21, a bending section 22, and a flexible tube section 23. The distal end hard section 21 is formed at a distal end of the insertion unit 20. The bending section 22 is connected to a proximal end of the distal end hard section 21 and is configured to bend. The flexible tube section 23 is connected to a proximal end of the bending section 22 and has flexibility.

A lighting unit 25 and an observation unit 26 are exposed and provided at a distal end surface of the distal end hard section 21. The lighting unit 25 has a light-emitting device such as an LED or the like. The observation unit 26 has an image sensor such as a CCD or the like. A distal end of the introduction channel 11 mentioned above has an opening formed in a distal end surface of the distal end hard section 21, and the introduction channel 11 extends to the manipulation unit 30 via the insertion unit 20.

A manipulation wire (not shown) is inserted into the insertion unit 20 so as to be able to advance and retract. As the manipulation wire is advanced and retracted, the bending section 22 can bend in a desired direction. While not shown, a power line configured to supply power to the lighting unit 25 and the like and a signal line configured to transmit image data acquired by the image sensor are provided in the insertion unit 20.

The manipulation unit 30 has a manipulation unit main body 31, a forceps port 32, and pluralities of dials 33 and buttons 34. The forceps port 32 is provided at a distal side of the manipulation unit main body 31. The pluralities of dials 33 and buttons 34 are provided at a proximal side of the manipulation unit main body 31. The forceps port 32 is in communication with an opening of a proximal side of the introduction channel 11. The pluralities of dials 33 and buttons 34 are provided at the proximal side of the manipulation unit main body 31. As the each dial 33 is rotated, the manipulation wire can be manipulated to bend the bending section 22. As the each button 34 is pressed, the lighting unit 25 or the observation unit 26 can be manipulated.

A universal cable 36 is connected to the manipulation unit main body 31. The universal cable 36 is connected to a display and a power supply apparatus (not shown). The power supply apparatus is connected to the lighting unit 25 via the power line. The display can display image data transmitted via the signal line as an image.

Figure 2:
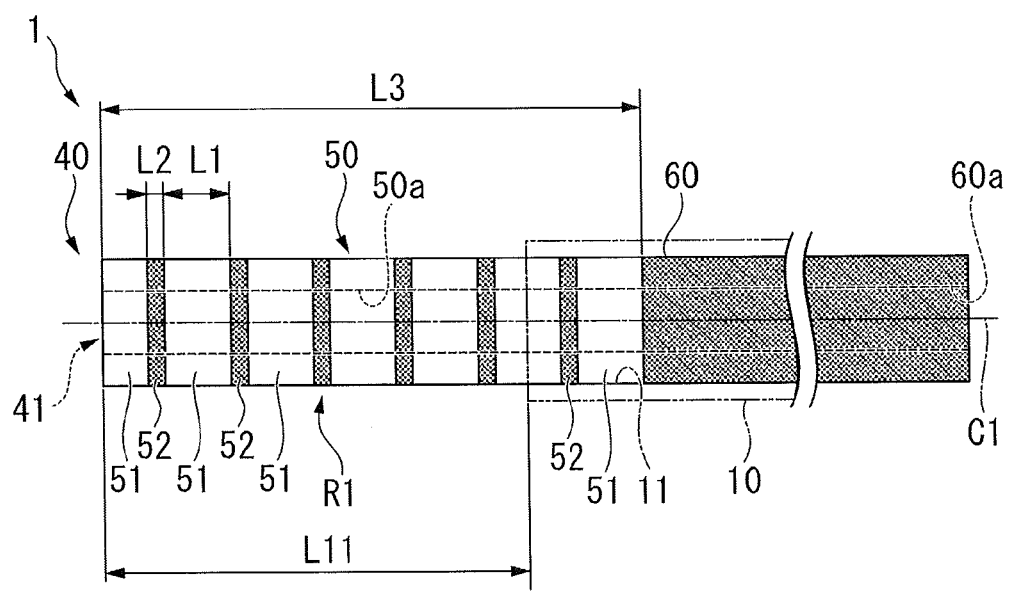
FIG. 2 is a side view of a guide sheath of the endoscope system according to the first embodiment of the present invention.
Figure 3:
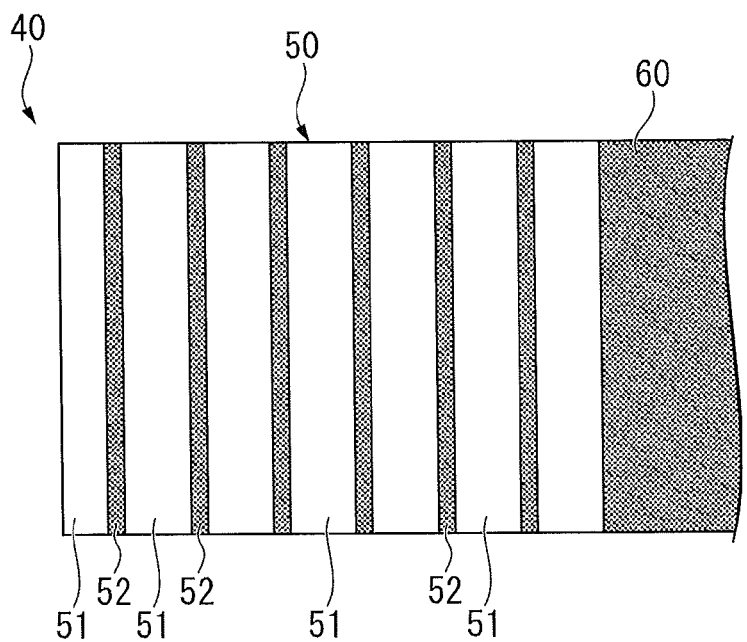
FIG. 3 is a development view of a distal side of the guide sheath of the endoscope system according to the first embodiment of the present invention.

The guide sheath 40 is used as a guide for guiding a distal end of a medical device such as a treatment tool or the like to a target area in a body. As shown in FIGS. 2 and 3, the guide sheath 40 has a bent section 50 and a support section (a proximal side hard section) 60. The bent section 50 is provided at a distal side of the guide sheath 40 and is configured to be bent in accordance with an external force. The support section 60 is provided at a proximal side of the bent section 50 and has flexibility. Each of the bent section 50 and the support section 60 is formed in a tubular shape. That is, the guide sheath 40 extends along an axis C1, which is a longitudinal axis thereof.

The bent section 50 is configured such that a soft section 51 and a hard section (a first hard section and a second hard section) 52 are alternately disposed in a direction of the axis C1 of the bent section 50 (a longitudinal direction). The soft section 51 is formed of a material having flexibility in an annular shape. The hard section 52 is formed in an annular shape and has bending stiffness larger than that of the soft section 51. The soft section 51 and the hard section 52 have the same outer diameter and the same inner diameter. In the direction of the axis C1, a length L1 of the soft section 51 is larger than a length L2 of the hard section 52. In the embodiment, seven soft sections 51 and six hard sections 52 are alternately disposed in the direction of the axis C1 to constitute the bent section 50. An opening section 41 through which the medical device inserted into the bent section 50 can freely protrude and retract is formed in the soft section 51 at the most distal side.

The soft section 51 is formed of a kneading material obtained by kneading a thermoplastic resin and a cross-linking accelerator. For example, while a polyethylene resin, a polybutadiene resin, a thermoplastic aromatic ether aromatic ester resin, a thermoplastic ether amide resin, or the like, may be appropriately employed as the thermoplastic resin usable in the soft section 51, the material is not limited thereto. In addition, as the thermoplastic resin, one kind of resin may be solely used or a plurality of kinds of resins may be blended and used.

As the cross-linking accelerator which is used, for example, various kinds of polyfunctional monomers may be provided. As specific examples, a diacrylate-based compound such as diethylene glycol or the like, a dimethacrylate-based compound such as ethylene glycol dimethacrylate or the like, a triacrylate-based compound such as trimethylolpropane triacrylate or the like, a trimethacrylate-based compound such as trimethylolpropane trimethacrylate or the like, a triallyl cyanurate-based compound such as triallyl isocyanurate, triallyl cyanurate, or the like, diallyl malate, diallyl fumarate, epoxy acrylate, and so on, may be provided. Each of these resins may be solely used, or two or more kinds of these resins may be combined and used. A use ratio of the cross-linking accelerator is 1 to 20 weight percent, preferably, 3 to 10 weight percent, with respect to 100 weight percent of thermoplastic aromatic ether ester resin. The cross-linking accelerator can be selected within this range in accordance with necessary heat resistance performance or the like. In addition, the cross-linking accelerator may be unnecessary in the kneading material.

The hard section 52 is formed of a cross-linked material in which the thermoplastic resin is cross-linked by irradiating the kneading material with ionizing radiation. It is known that as the ionizing radiation is radiated to the kneading material, molecules of the thermoplastic resin are cross-linked and a modulus of elasticity of the resin is increased. As the ionizing radiation used in the embodiment, an electron beam, an accelerated electron beam, γ rays, X rays, α rays, β rays, ultraviolet rays, or the like, may be provided. In view of industrial concerns such as convenience of a radiation source, a penetration thickness of the ionizing radiation, a speed of the cross-linking treatment, or the like, the accelerated electron beam and the γ rays can be appropriately used. A voltage of the accelerated electron beam can be appropriately selected in accordance with a thickness of a specimen. In the embodiment, an exposure dose of the ionizing radiation is set to, for example, 500 kilograys (kGy) or more. In addition, in all of the drawings after FIG. 1, the same hatching is shown on the members formed of the cross-linked material.

The soft section 51 and the hard section 52 have the same cross-sectional shape in a plane perpendicular to the axis C1. However, since the modulus of elasticity of the cross-linked material that forms the hard section 52 is larger than that of the kneading material that forms the soft section 51, bending stiffness of the hard section 52 is larger than that of the soft section 51. The modulus of elasticity of the cross-linked material is preferably equal to or more than three times that of the kneading material.

In the embodiment, the support section 60 is formed of the above-mentioned cross-linked material in a tubular shape, and is provided at the entire circumference in a circumferential direction of the bent section 50. The support section 60 and the bent section 50 have the same outer diameter and the same inner diameter. Bending stiffness of the support section 60 is larger than that of the soft section 51. A conduit line 60a of the support section 60 is in communication with a conduit line 50a of the bent section 50. A channel of the guide sheath 40 is constituted by the conduit lines 50a and 60a. The channel is in communication with the above-mentioned opening section 41. As an example of dimensions of the guide sheath 40, an outer diameter is 2.5 mm, an inner diameter is 2.1 mm, and a length is about 1000 mm. An index configured to show a protrusion length of the distal side of the guide sheath 40 from the introduction channel 11 of the endoscope 10 is preferably formed at an outer circumferential surface of the support section 60.

The guide sheath 40 having the above-mentioned configuration is used in a state in which the distal side of the guide sheath 40 protrudes from the introduction channel 11 of the endoscope 10 as shown in FIG. 2. In the guide sheath 40, a length L11 of a protrusion R1, which protrudes from the introduction channel 11, in the direction of the axis C1 is about 5 cm to 20 cm, depending on individual differences in patients. A length L3 of the bent section 50 in the direction of the axis C1 is larger than the length L11 by 1 cm or more. In the embodiment, at least the soft section 51 and the pair of hard sections 52 disposed to sandwich the soft section 51 in the direction of the axis C1 are disposed in the bent section 50. The length of the guide sheath 40 is set such that the proximal end section of the guide sheath 40 protrudes from the forceps port 32 to the proximal side regardless of the above-mentioned length L11.

Figure 4:
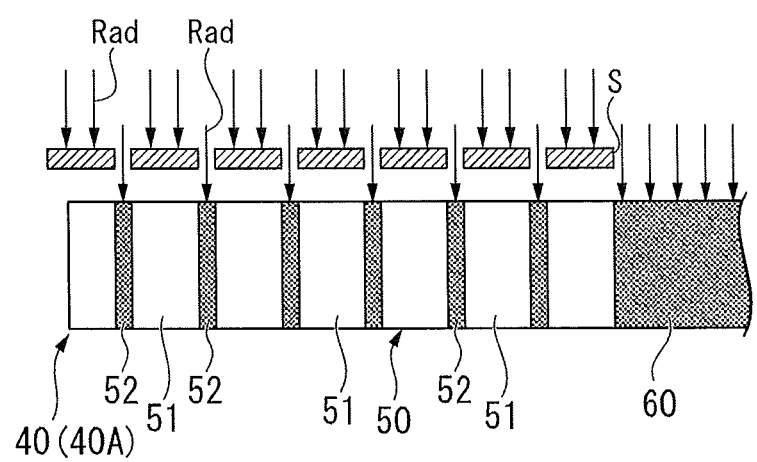
FIG. 4 is a view for describing a procedure of cross-linking a portion of the guide sheath of the endoscope system according to the first embodiment of the present invention to form a cross-linked material.

In manufacturing the guide sheath 40 having the above-mentioned configuration, first, as shown in FIG. 4, a sheath 40A formed of the above-mentioned kneading material in the same tubular shape as the guide sheath 40 is prepared.

A portion of the sheath 40A that is not intended to be cross-linked is covered by a shield S made of lead or the like, and ionizing radiation Rad is radiated to the sheath 40A. Accordingly, a region irradiated with the ionizing radiation Rad is cross-linked to become the cross-linked material, and the hard section 52 and the support section 60 are formed. Since a region covered by the shield S is not cross-linked, the region becomes the soft section 51 formed of the kneading material in which properties of the thermoplastic resin remain. Accordingly, as a position or a length of the region covered by the shield S is appropriately set, the cross-linked material can be formed at a desired position and length of the sheath 40A.

Figure 5:
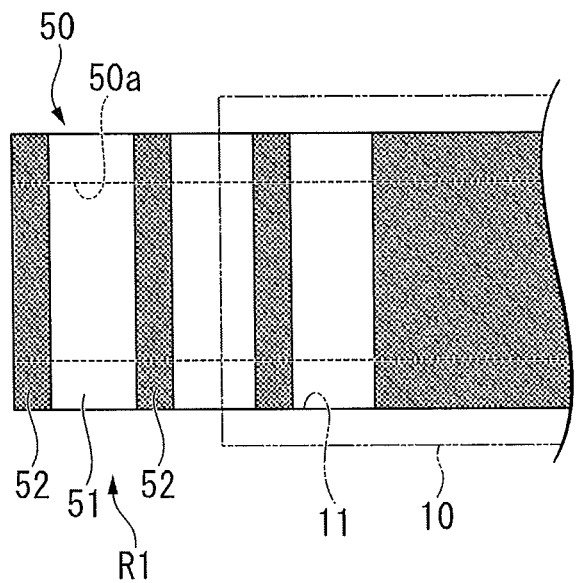
FIG. 5 is a view for describing a state before a protrusion of the guide sheath of the endoscope system according to the first embodiment of the present invention receives an external force.

Next, an operation of the endoscope system 1 having the above-mentioned configuration is described. Before describing an example of a specific procedure, an action when the protrusion R1 protruding from the introduction channel 11 in the guide sheath 40 receives an external force is described in detail. Hereinafter, as shown in FIG. 5, a model is simplified, and the description focuses on movement of the soft section 51 and the pair of hard sections 52 disposed at the protrusion R1. First, the case in which the protrusion R1 receives such an external force to be bent is described.

Figure 6:
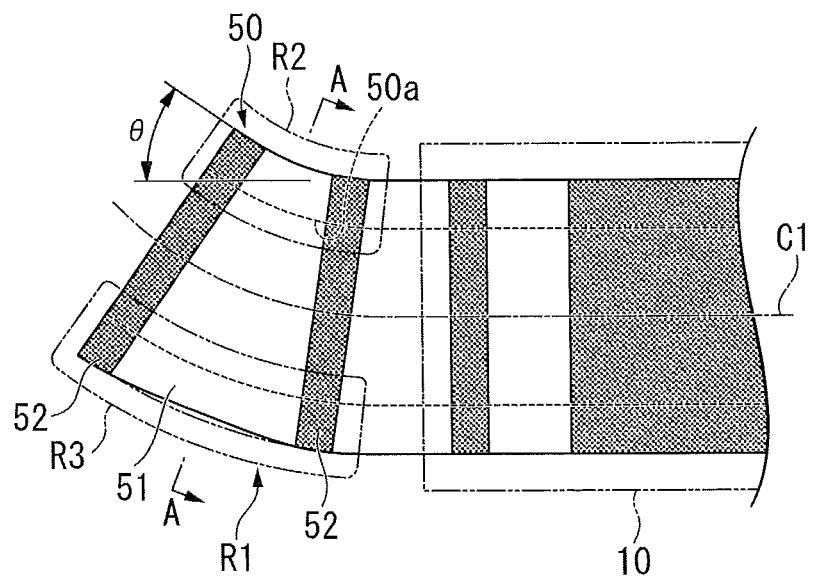
FIG. 6 is a view for describing a state in which the protrusion of the guide sheath of the endoscope system according to the first embodiment of the present invention receives the external force to be bent.
Figure 7:
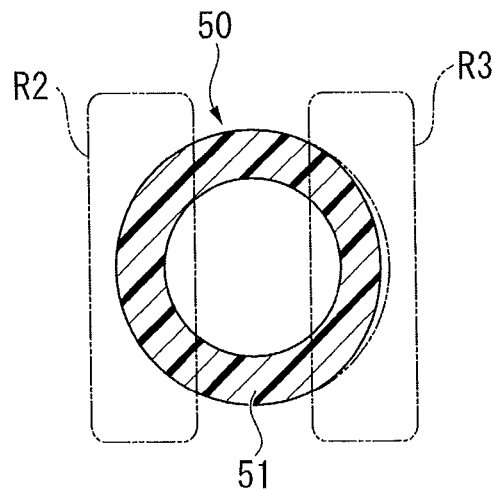
FIG. 7 is a cross-sectional view taken along line A-A of FIG. 6.

As shown in FIGS. 6 and 7, when the protrusion R1 is bent, an inner range R2 that is an inner side of a curvature in the soft section 51 and the hard sections 52 is compressed in the direction of the axis C1. Meanwhile, an outer range R3 that is an outer side of the curvature in the soft section 51 and the hard sections 52 is pulled in the direction of the axis C1 and is compressed in the radial direction. The deformation of the soft section 51 is remarkably larger than that of the hard section 52 due to a difference in bending stiffness. As a result, a cross-sectional shape of the soft section 51 perpendicular to the axis C1 is substantially an elliptical shape. Even when the cross-sectional shape of the soft section 51 is deformed in the elliptical shape at a central portion in the direction of the axis C1, both ends of the soft section 51 in the direction of the axis C1 are supported by the hard sections 52 with little deformation.

Here, when the bent section 50 bent once is returned to its original straight shape, a plastic strain concaved toward the conduit line 50a remains at a bent portion of the bent section 50, which is defined as "kink." A bending angle θ at which the bent section 50 starts to kink is referred to as a "kink angle." When the bent section 50 is kinked, the treatment tool cannot be easily inserted into the conduit line 50a of the bent section 50.

In the bent section 50 according to the embodiment, the kink of the soft section 51 and destruction of the conduit line 50a are prevented by the pair of hard sections 52 disposed to sandwich the soft section 51. Since the bending stiffness of the soft section 51 is relatively small, the bent section 50 can be easily bent. Since the length L1 of the soft section 51 is set to be longer than the length L2 of the hard section 52, the bent section 50 is easily bent. Since each of the soft section 51 and the hard section 52 is formed in an annular shape, deformation of the bent section 50 is uniform around the axis C1.

Since the bending stiffness of the support section 60 is larger than that of the soft section 51, the support section 60 is prevented from being bent when the operator pushes the support section 60 thereinto, and the pushing force is securely applied to the bent section 50 via the support section 60. The protrusion R1 may receive an external force to be compressed in the direction of the axis C1. In this case, basically, since the soft section 51 is merely deformed in the direction of the axis C1, probability of the kink is small in comparison with the case in which the protrusion R1 is bent.

Figure 8:
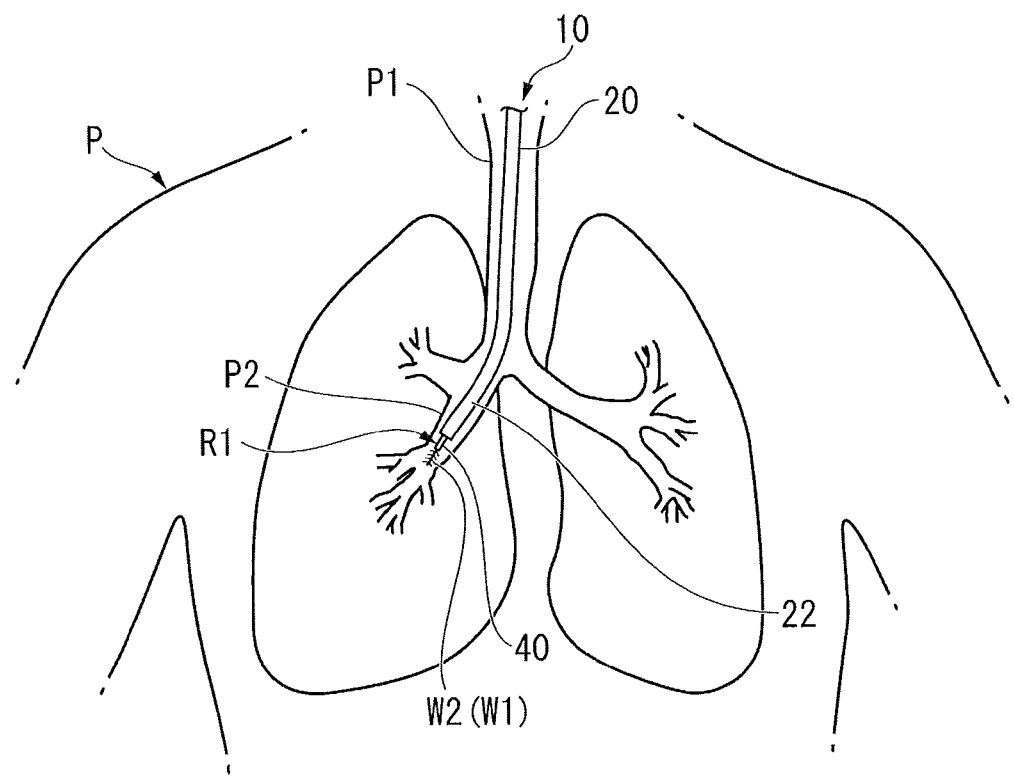
FIG. 8 is a view for describing a procedure using the endoscope system according to the first embodiment of the present invention.

Next, an operation of the endoscope system 1 when the insertion unit 20 is inserted into the bronchial tube (the target area) of the patient and the procedure is endoscopically performed using several treatment tools is described. The operator presses the button 34 to supply power to the lighting unit 25 and illuminate ahead of the insertion unit 20. The operator recognizes an image acquired by the observation unit 26 through a display. As shown in FIG. 8, the operator inserts the insertion unit 20 of the endoscope 10 into the bronchial tube P2 from the mouth of a patient P through the trachea P1. The operator moves the distal end of the insertion unit 20 to the vicinity of the treatment target tissue while rotating the dial 33 and bending the bending section 22 as necessary.

The operator inserts an ultrasonic probe (a medical device) (not shown) into the guide sheath 40 from the proximal end of the guide sheath 40 at the outside of the patient P. The operator inserts the guide sheath 40, through which the ultrasonic probe is inserted, into the introduction channel 11 through the forceps port 32 using the bent section 50 as the distal side. The operator adjusts the length L11 of the guide sheath 40 protruding from the introduction channel 11 while checking the display and the index. The operator pushes the ultrasonic probe into the guide sheath 40 and makes the ultrasonic probe protrude from the distal end of the guide sheath 40 in a state in which the position of the guide sheath 40 with respect to the introduction channel 11 is maintained. The operator finds the treatment target tissue using the ultrasonic probe and specifies a position of the treatment target tissue.

Figure 9:
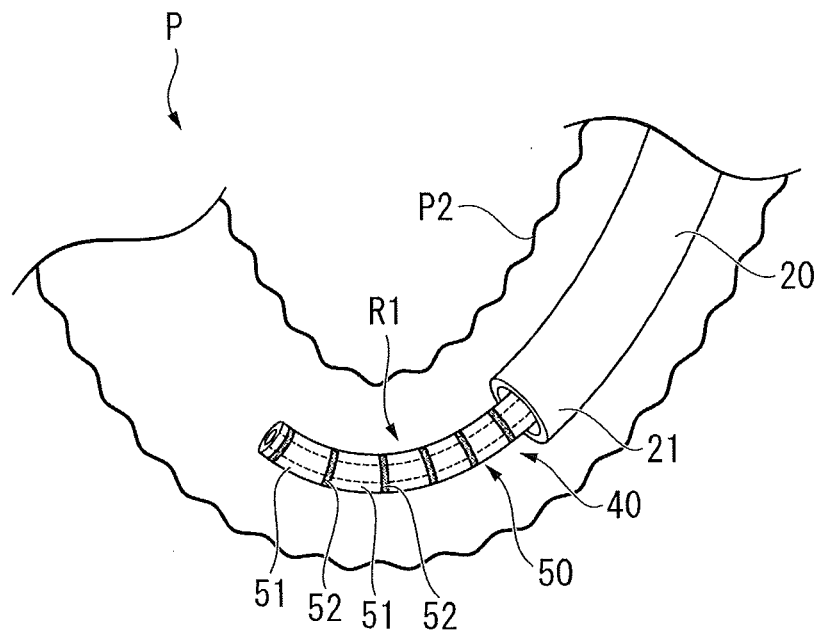
FIG. 9 is a view for describing a state in which the protrusion of the guide sheath of the endoscope system according to the first embodiment of the present invention receives the external force from the bronchial tube.

The operator pulls the ultrasonic probe from the guide sheath 40. Here, the treatment tool or the like is not inserted into the guide sheath 40. For this reason, when the protrusion R1 of the guide sheath 40 comes in contact with the tissue of the bronchial tube P2 or the like, the protrusion R1 mainly bears the external force. Even in this case, as shown in FIG. 9, the protrusion R1 can bear the external force without kinking. In this state, the treatment tool can pass through the guide sheath 40. In addition, when the insertion unit 20 is inserted into the bronchial tube P2, the external force may be applied to bend the protrusion R1 even by breathing or movement of muscles of the patient P as well as when the protrusion R1 comes in contact with the tissue.

Figure 10:
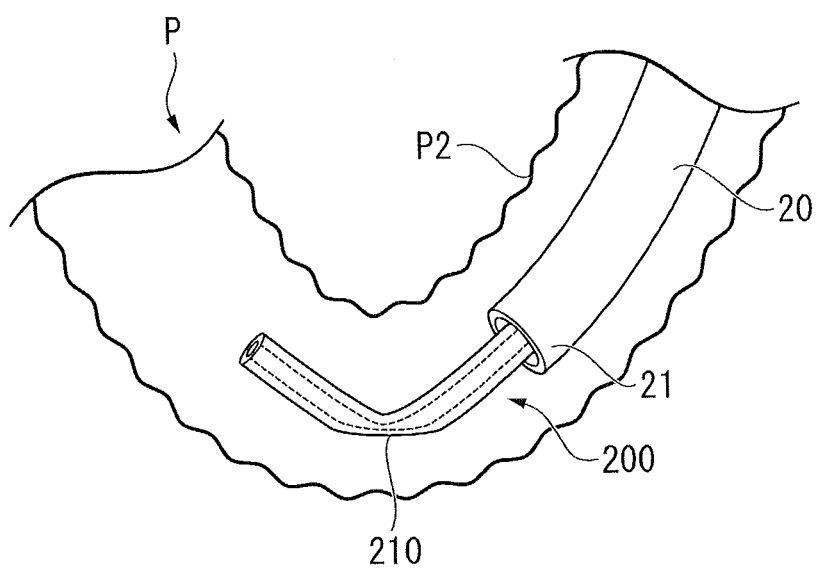
FIG. 10 is a view for describing a state in which the conventional guide sheath serving as a comparative example receives an external force from the bronchial tube.

On the other hand, as a comparative example, as shown in FIG. 10, the case in which a conventional guide sheath 200 is used instead of the guide sheath 40 according to the embodiment is described. The entire bent section 210 of the guide sheath 200 of the comparative example is formed of a kneading material. In this case, a portion of the bent section 210 protruding from the insertion unit 20 is bent by the external force of the bronchial tube P2 and kinked. The treatment tool cannot pass through the kinked guide sheath 200.

Again, the procedure is described. The operator inserts a brush-type treatment tool (a medical device) W1 into the guide sheath 40 from the proximal end of the guide sheath 40. As shown in FIG. 8, the operator causes a brush section W2 of the brush-type treatment tool W1 to protrude from the distal end of the guide sheath 40 and collects the tissue using the brush section W2. The operator pulls the brush-type treatment tool W1 from the guide sheath 40 to obtain the tissue. The operator inserts a biopsy forceps or the like (not shown) into the guide sheath 40 from the proximal end of the guide sheath 40 and performs appropriate treatment. The operator pulls the biopsy forceps from the guide sheath 40. The operator pulls the guide sheath 40 and the insertion unit 20 from the mouth of the patient P to terminate a series of procedures.

As described above, according to the guide sheath 40 and the endoscope system 1 according to the embodiment, the bent section 50 is configured such that the soft sections 51 and the hard sections 52 are alternately disposed in the direction of the axis C1. Since the bending stiffness of the soft section 51 is relatively small, the bent section 50 can be bent easily, and flexibility of the bent section 50 is maintained. Since the hard sections 52 support the soft sections 51 deformed to be crushed in the radial direction when the bent section 50 is bent, the bent section 50 cannot be easily kinked. Accordingly, the treatment tool can be easily inserted into the conduit line 50a of the bent section 50, which is bent.

The soft section 51 is formed of a kneading material. The hard section 52 is formed of a cross-linked material. For this reason, even when a shape of the hard section 52 is complicated, the hard section 52 can be easily formed in a desired shape by adjusting the shape of the shield S. In a state in which the outer diameter and the inner diameter are uniform in the direction of the axis C1, the modulus of elasticity of the kneading material can be varied by the ionizing radiation. Accordingly, the guide sheath 40 can be configured to be easily guided by the introduction channel 11 of the endoscope 10. The guide sheath 40 can be configured in a shape in which the treatment tool or the like inserted through the channel of the guide sheath 40 easily passes through the bent section 50 to be guided to the distal end section. Since each of the soft section 51 and the hard section 52 is formed in an annular shape, deformation of the bent section 50 is uniform around the axis C1, and the operator can easily manipulate the bent section 50.

The bending stiffness of the support section 60 is larger than that of the soft section 51. For this reason, as the soft section 51 is deformed when the operator pushes the support section 60 thereinto, the support section 60 can be prevented from being bent. Then, the pushing force can be securely applied to the bent section 50 via the support section 60, and an insertion property of the guide sheath 40 can be increased. Since a proximal side hard section formed of a cross-linked material is provided at the support section 60, a force applied to the support section 60 can be securely applied to the bent section 50. Since the support section 60 is formed of a cross-linked material throughout the entire circumference around the axis C1, the force applied to the support section 60 can be securely applied to the bent section 50 regardless of a position in the circumferential direction.

In the direction of the axis C1, the length L1 of the soft section 51 is larger than the length L2 of the hard section 52. For this reason, displacement of the soft section 51 that can be deformed in the direction of the axis C1 is increased, and the bent section 50 can be more easily bent. The length L3 of the bent section 50 is larger than the length L11 of the protrusion R1. Accordingly, a portion of the guide sheath 40 protruding from the introduction channel 11 cannot be easily kinked in a secure manner. The endoscope system 1 according to the embodiment includes the endoscope 10 and the guide sheath 40. Accordingly, the length L11 of the protrusion R1 of the guide sheath 40 can be checked by the endoscope 10.

In the embodiment, the bent section 50 is constituted by the seven soft sections 51 and the six hard sections 52. However, in the bent section, as long as at least one soft section 51 and the pair of hard sections 52 disposed to sandwich the soft section 51 in the direction of the axis C1 are provided, the numbers of the soft sections 51 and the hard sections 52 are not particularly limited.

Second Embodiment

Next, a second embodiment of the present invention is described with reference to FIGS. 11 to 14. The same elements as in the above embodiment are designated by the same reference numerals and description thereof is omitted, and only different points are described.

Figure 11:
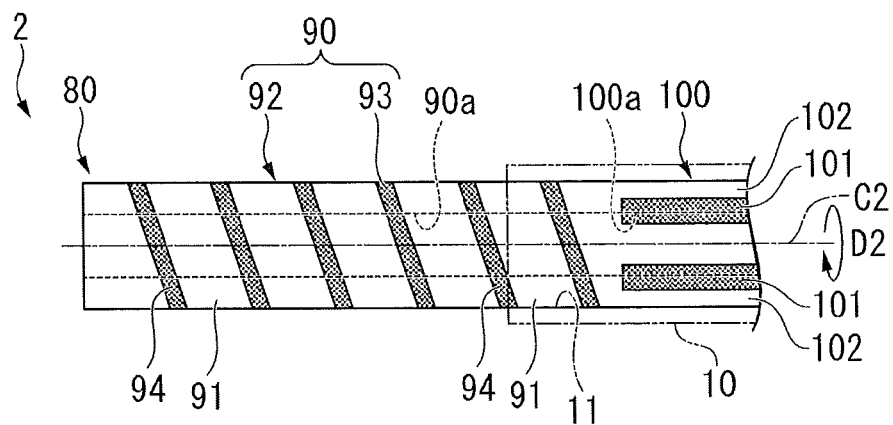
FIG. 11 is a side view of a distal side of an endoscope system according to a second embodiment of the present invention.
Figure 12:
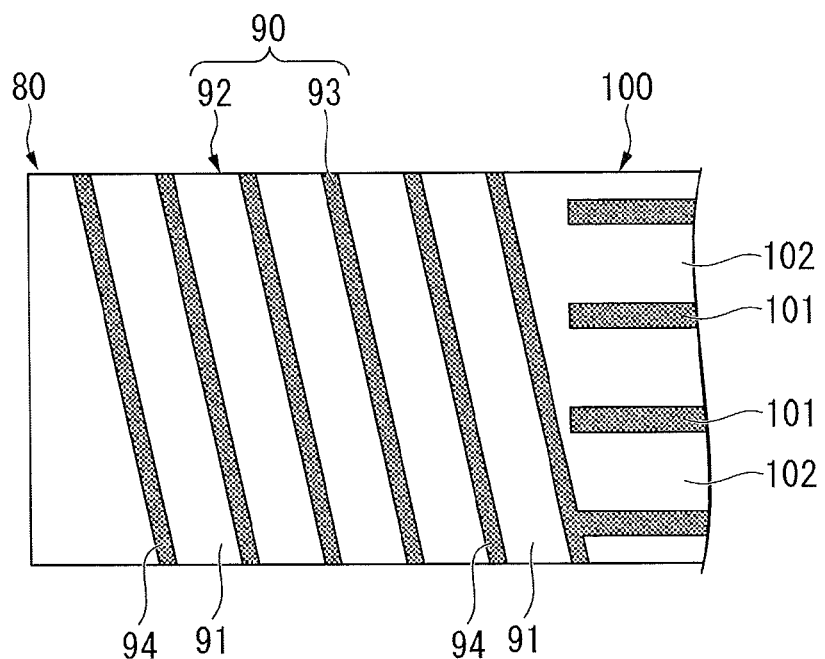
FIG. 12 is a development view of a distal side of a guide sheath of the endoscope system according to the second embodiment of the present invention.

As shown in FIGS. 11 and 12, an endoscope system 2 according to the embodiment includes a guide sheath 80 instead of the guide sheath 40 of the endoscope system 1 of the first embodiment. The guide sheath 80 has a bent section 90 and a support section 100. The bent section 90 is disposed at the distal side upon passing through the introduction channel 11. The support section 100 is provided at the proximal side of the bent section 90.

The bent section 90 has a soft section 92 and a hard section (first hard section, second hard section) 93. The soft section 92 is formed by spirally winding a linear body 91 formed of the above-mentioned kneading material around an axis C2 of the guide sheath 80. The hard section 93 is disposed between the neighboring linear bodies 91 in a direction of the axis C2, and is formed in a spiral shape. The hard section 93 is formed of the above-mentioned cross-linked material. The linear body 91 and a linear body 94 that constitutes the hard section 93 are alternately disposed in the direction of the axis C2. The soft section 92 and the hard section 93 have the same outer diameter and the same inner diameter. In the embodiment, the linear body 91 is spirally wound around the axis C2 about seven times to form the soft section 92. The linear body 94 is spirally wound around the axis C2 about six times to form the hard section 93. The bent section 90 is formed in a shape in which at least the linear body 91 is spirally disposed around the axis C2 throughout one circumference and the linear bodies 94 are disposed to sandwich the linear body 91 in the direction of the axis C2.

The support section 100 is formed to extend in the direction of the axis C2. The support section 100 has four proximal side hard sections 101 and four proximal side soft sections 102. The proximal side hard sections 101 are disposed to be spaced apart from each other in a circumferential direction D2 of the bent section 90. The proximal side soft section 102 is disposed between the neighboring proximal side hard sections 101 in the circumferential direction D2. The proximal side hard section 101 is formed of the above-mentioned cross-linked material. The proximal side soft section 102 is formed of the above-mentioned kneading material. The support section 100 constituted by the four proximal side hard sections 101 and the four proximal side soft sections 102 is formed in a tubular shape. The support section 100 and the bent section 90 have the same outer diameter and the same inner diameter. A conduit line 100a of the support section 100 is in communication with a conduit line 90a of the bent section 90.

The bent section 90 of the guide sheath 80 according to the embodiment is configured not to be easily kinked while maintaining flexibility by the same action as the bent section 50 of the above-mentioned first embodiment. Since the support section 100 is formed of the kneading material and the cross-linked material, the bending stiffness of the support section 100 is smaller than that of the hard section 93 formed of the cross-linked material only. The guide sheath 80 according to the embodiment may be manufactured in the same manner as the guide sheath 40 of the first embodiment by adjusting a shape of the shield.

Figure 13:
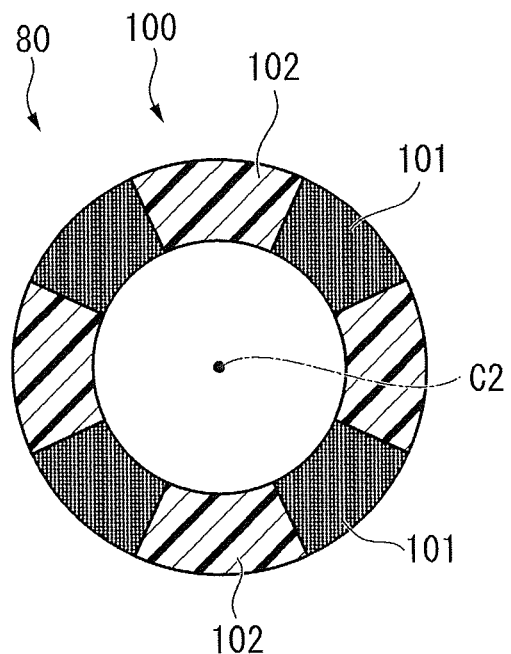
FIG. 13 is a cross-sectional view in a natural state of a support section of the guide sheath of the endoscope system according to the second embodiment of the present invention.
Figure 14:
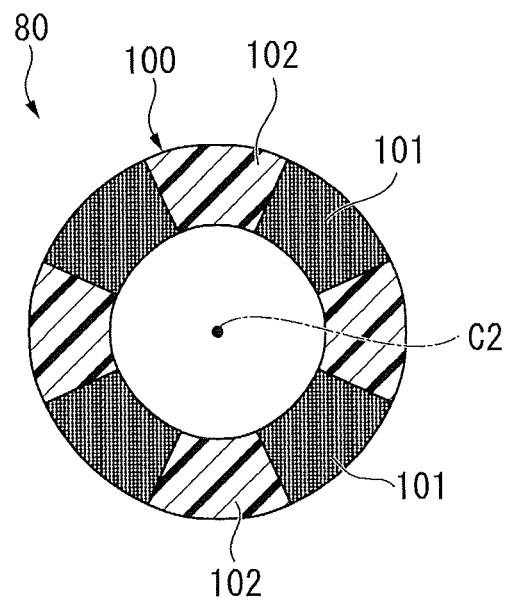
FIG. 14 is a cross-sectional view when the support section of the guide sheath of the endoscope system according to the second embodiment of the present invention receives a pressing force.

In the support section 100 of the guide sheath 80, in a natural state in which no external force other than gravity is applied, a cross-sectional shape of a plane perpendicular to the axis C2 is a circular shape as shown in FIG. 13, and each of the proximal side hard section 101 and the proximal side soft section 102 has an arc shape. When a pressing force is applied to an outer circumferential surface of the support section 100, as shown in FIG. 14, there is little deformation of the proximal side hard section 101 due to a difference in modulus of elasticity, and the support section 100 is reduced in diameter as the proximal side soft section 102 is compressed. Similarly, when the pressing force is released, the support section 100 is increased in diameter as the proximal side soft section 102 is deformed to be expanded outward.

According to the guide sheath 80 and the endoscope system 2 according to the embodiment having the above-mentioned configuration, the bent section 90 can be configured not to be easily kinked while flexibility of the bent section 90 is maintained. Since the bending stiffness of the support section 100 is smaller than that of the hard section 93, the support section 100 is more largely deformed than the hard section 93 by a reaction force from the tissue, and buckling of the hard section 93 can be prevented. Since the support section 100 is constituted by the proximal side hard sections 101 and the proximal side soft sections 102, the support section 100 can be easily reduced or increased in diameter.

Third Embodiment

Next, a third embodiment of the present invention is described with reference to FIGS. 15 to 17. The same elements as in the above embodiments are designated by the same reference numerals and description thereof is omitted, and only different points are described.

Figure 15:
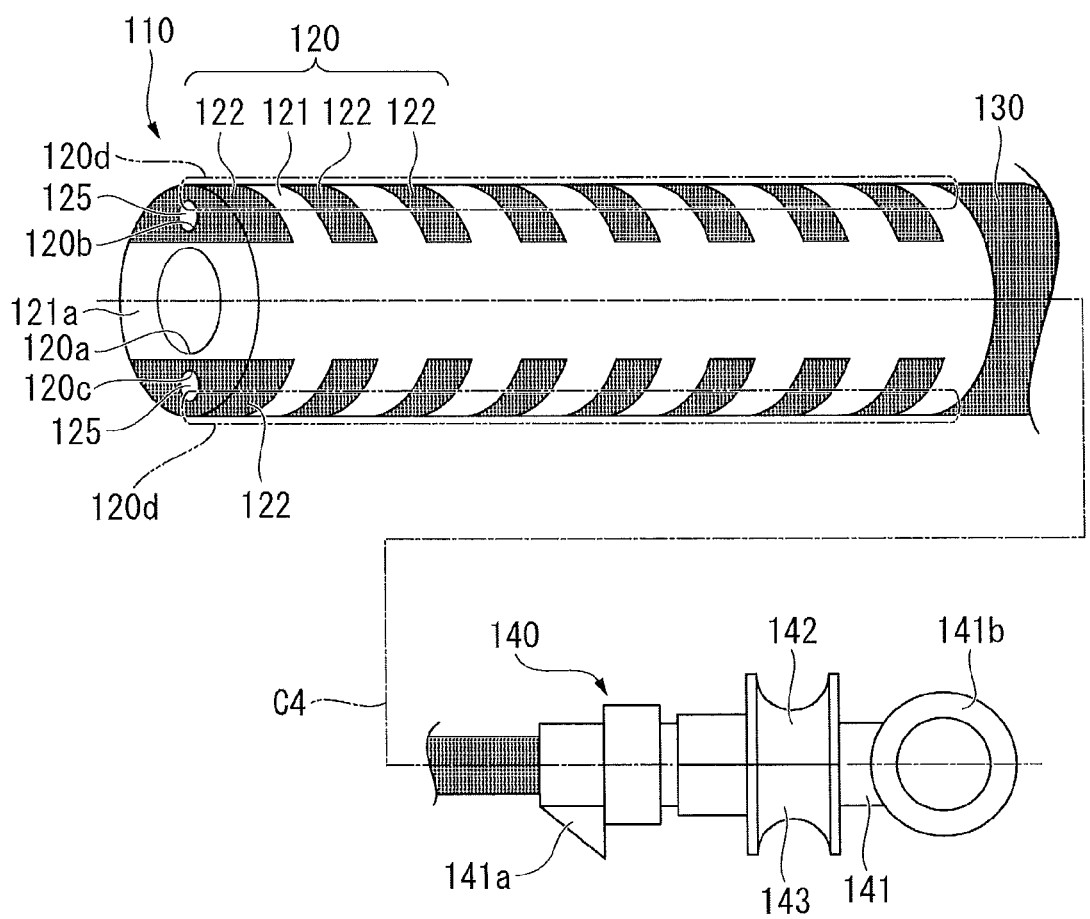
FIG. 15 is an overall view of a guide sheath according to a third embodiment of the present invention.
Figure 16:
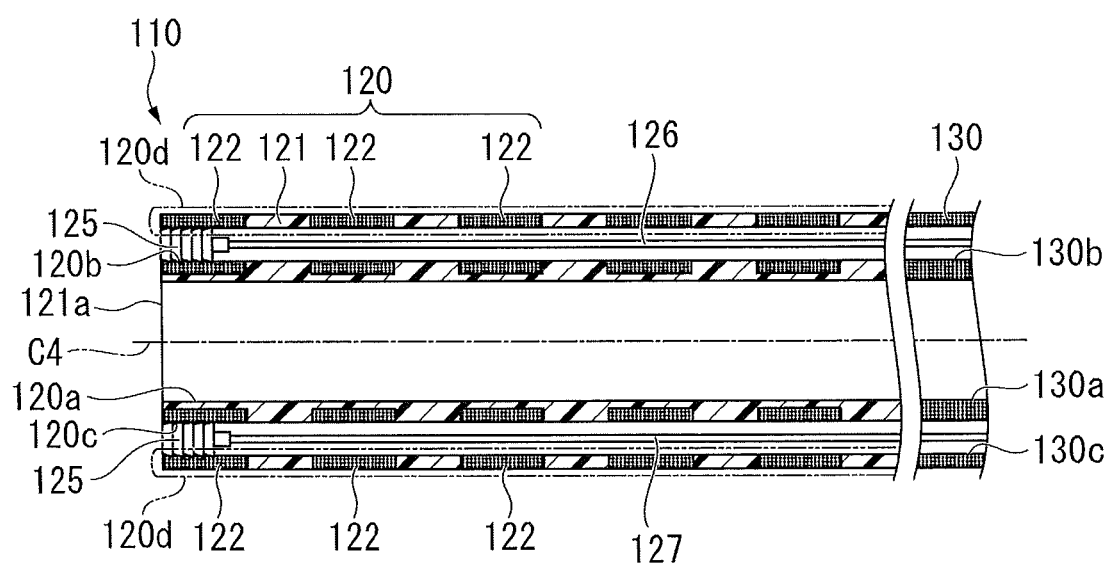
FIG. 16 is a cross-sectional view of a distal side of the guide sheath according to the third embodiment of the present invention.
Figure 17:
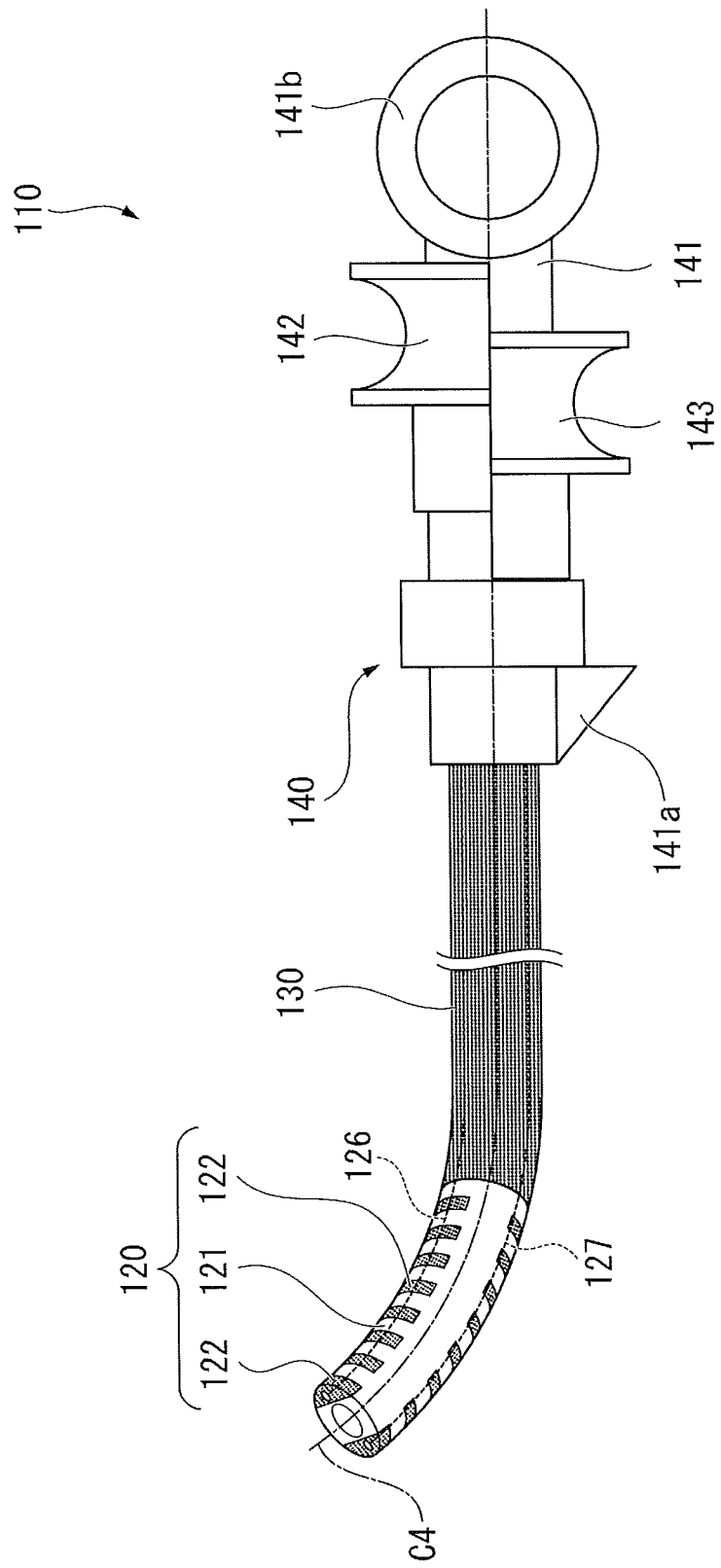
FIG. 17 is a view for describing a state when the guide sheath according to the third embodiment of the present invention is bent.

As shown in FIGS. 15 and 16, a guide sheath 110 according to the embodiment has a bent section 120, a support section (a proximal side hard section) 130, and a manipulation unit 140. The bent section 120 is provided at a distal side of the guide sheath 110, and configured to be bent in accordance with an external force. The support section 130 is provided at a proximal side of the bent section 120, and has flexibility. The manipulation unit 140 is provided at a proximal side of the support section 130, and is configured to bend the bent section 120. Each of the bent section 120 and the support section 130 is formed in a tubular shape.

A first bent section side conduit line 120a and second bent section side conduit lines 120b and 120c extending in a longitudinal direction of the guide sheath 110 are formed at the bent section 120. The first bent section side conduit line 120a is formed on a central axis C4 of the guide sheath 110. The second bent section side conduit lines 120b and 120c have a smaller diameter than the first bent section side conduit line 120a, and are configured to sandwich the first bent section side conduit line 120a. That is, the second bent section side conduit lines 120b and 120c are formed on a position displaced from the central axis C4 in a radial direction of the guide sheath 110.

The bent section 120 is configured by disposing a plurality of hard sections (a first hard section and a second hard section) 122 on a soft section 121, which is formed in a tubular shape, at predetermined intervals in a longitudinal direction. The hard section 122 is formed in a plate shape, which is a substantially semi-circular shape when seen in the longitudinal direction in parallel. The hard sections 122 are disposed to sandwich the central axis C4. The hard sections 122 are also provided at a distal end surface 121a of the soft section 121. The soft section 121 is formed of a kneading material obtained by kneading a thermoplastic resin and a cross-linking accelerator, like the above-mentioned soft section 51. As the thermoplastic resin, for example, a low-density polyethylene resin (LDPE) can be appropriately used. As the cross-linking accelerator, triallyl isocyanurate can be appropriately used. The hard section 122 is formed by radiating the ionizing radiation to the kneading material and cross-linking the material as described above. Hardness and breaking strength of the hard section 122 are larger than those of the soft section 121.

A manipulation wire tip (a fixing member) 125 is fixed to a distal end section of each of the second bent section side conduit lines 120b and 120c. The manipulation wire tip 125 may be formed of a metal such as stainless steel or the like, a hard resin, or the like. The manipulation wire tip 125 is fixed to the hard section 122 provided at the distal end surface 121a of the soft section 121 constituting the second bent section side conduit lines 120b and 120c by being fitted into the second bent section side conduit lines 120b and 120c.

Manipulation wires 126 and 127 are disposed in the second bent section side conduit lines 120b and 120c, respectively. Distal end sections of the manipulation wires 126 and 127 are fixed to the manipulation wire tips 125. That is, the distal end sections of the manipulation wires 126 and 127 are fixed to the cross-linked hard section 122 by the manipulation wire tips 125. For this reason, split or rupture of the bent section 120 in the vicinity of each of the manipulation wire tips 125 and split or rupture of a distal end section of each partition wall 120d between the second bent section side conduit lines 120b and 120c and the outer circumferential surface of the bent section 120 to which the manipulation wires 126 and 127 are fixed can be prevented. Here, the partition walls 120d mean a portion which ranges throughout the bent section 120 located between the outer circumferential surface of the bent section 120 and the second bent section side conduit line 120b and a portion which ranges throughout the bent section 120 located between the outer circumferential surface of the bent section 120 and the second bent section side conduit line 120c. In addition, the distal end sections of the manipulation wires 126 and 127 may be directly fixed to the hard section 122 provided at the distal end surface 121a without providing the manipulation wire tips 125 at the distal end sections of the second bent section side conduit lines 120b and 120c.

The support section 130 has a cross-section of a plane perpendicular to the longitudinal direction, which is formed in the same shape as the bent section 120. That is, a first support section side conduit line 130a and second support section side conduit lines 130b and 130c extending in the longitudinal direction are formed at the support section 130. The support section 130 is formed by radiating the ionizing radiation to the kneading material obtained by kneading the thermoplastic resin such as a high-density polyethylene resin (HDPE) or the like and the cross-linking accelerator and cross-linking the kneading material. The bent section 120 and the support section 130 are adhered to each other by an adhesive agent. The bending stiffness of the bent section 120 is smaller than that of the support section 130. The first support section side conduit line 130a and the second support section side conduit lines 130b and 130c are in communication with the first bent section side conduit line 120a and the second bent section side conduit lines 120b and 120c, respectively. Second channels are constituted by the second bent section side conduit line 120b and the second support section side conduit line 130b, and the second bent section side conduit line 120c and the second support section side conduit line 130c, respectively.

The manipulation unit 140 has a known configuration. The manipulation unit 140 includes a manipulation unit shaft 141, and sliders 142 and 143. The manipulation unit shaft 141 is formed in a tubular shape, and is fixed to a proximal end section of the support section 130. The sliders 142 and 143 are provided at the manipulation unit shaft 141 so as to be slidable in the longitudinal direction. A main port 141a in communication with the first support section side conduit line 130a of the support section 130 is provided at a distal end section of the manipulation unit shaft 141. A thumb ring 141b is attached to a proximal end section of the manipulation unit shaft 141. While not shown, the sliders 142 and 143 are connected to the manipulation wires 126 and 127, respectively. The sliders 142 and 143 are configured to be independently slidable from each other.

In the guide sheath 110 configured as described above, the operator grips the manipulation unit 140 by hooking a thumb in the thumb ring 141b, and an index finger and a middle finger on the sliders 142 and 143. In a state in which the bent section 120 and the support section 130 are straight, as shown in FIG. 17, when the slider 142 is moved (retracted) to the proximal side in the longitudinal direction with respect to the manipulation unit shaft 141, the manipulation wire 126 is moved to the proximal side. The manipulation wire tip 125 fixed to the manipulation wire 126 is moved to the proximal side. The support section 130 having the large bending stiffness is not excessively deformed, the soft section 121 of the bent section 120 is compressed in the longitudinal direction, and thus the bent section 120 is bent such that the manipulation wire 126 side becomes inside. Here, the manipulation wire 126 abuts an inner surface of the partition wall 120d near the manipulation wire 126 throughout substantially the entire length of the bent section 120. Since the plurality of hard sections 122 are provided at the bent section 120, splitting of the partition wall 120d near the manipulation wire 126 and escape of the manipulation wire 126 when the manipulation wire 126 is pulled to the proximal side to bend the bent section 120 can be prevented. When the slider 142 is moved to the distal side with respect to the manipulation unit shaft 141, the bent section 120 and the support section 130 are returned to the straight state. Similarly, when the slider 143 is moved to the proximal side in the longitudinal direction, the bent section 120 is bent toward the manipulation wire 127.

According to the guide sheath 110 according to the embodiment having the above-mentioned configuration, the bent section 120 can be configured not to be easily kinked while flexibility of the bent section 120 is maintained. As the hard sections 122 are provided at the bent section 120, the manipulation wires 126 and 127 can be retracted without damage to the partition walls 120d of the bent section 120. The distal end sections of the manipulation wires 126 and 127 are fixed to the hard sections 122 via the manipulation wire tips 125, respectively. Since the bending stiffness of the hard section 122 is larger than that of the soft section 121, the manipulation wire tips 125 can be prevented from slipping through the bent section 120, and the distal end sections of the manipulation wires 126 and 127 can be securely fixed to the bent section 120. Since the bent section 120 and the support section 130 have a constant outer diameter regardless of a position in the longitudinal direction, concave and convex portions are not formed in the outer circumferential surfaces of the bent section 120 and the support section 130.

In the embodiment, the guide sheath 110 includes the manipulation unit 140. However, the guide sheath 110 may not include the manipulation unit 140, because the bent section 120 can be bent by retracting the manipulation wires 126 and 127 with respect to the support section 130.

In the first embodiment to the third embodiment, an additive for improving toughness of a soft material may be included in the kneading material. In addition, the "toughness" mentioned here has the same meaning as brittleness and a property of remarkable extension or contraction deformation when the material is pulled. "Improving the toughness" means that the material can be easily expanded or contracted.

As the above-mentioned additive, high-density polyethylene (HDPE), low-density polyethylene (LDPE), ethylene-vinyl acetate (EVA), carbon, and a combination thereof may be appropriately selected and used. As the above-mentioned additive is included in the kneading material, a decrease in toughness (the kneading material cannot be easily expanded) due to excessive cross-linking of the kneading material can be prevented.

In the axial direction, a length of the soft section may be set to be equal to or smaller than that of the hard section. These lengths may be appropriately set based on the bending angle θ of the bent section, or the like. When the bending stiffness of the support section is intended to be increased, a cross-linking ratio of the support section may be increased or a reinforcement member may be attached to an outer or inner surface of the support section.

In the first embodiment to the third embodiment, the insertion unit 20 of the endoscope system is inserted into the lung through the mouth of the patient P. However, an area into which the insertion unit 20 is inserted is not limited to the lung but may be, for example, a hollow organ such as the esophagus, the duodenum, the small intestine, the large intestine, the uterus, the bladder, a blood vessel, and so on.

While the internal introduction device is the endoscope, the internal introduction device is not limited to the endoscope but may be, for example, an over tube or the like.

Hereinabove, while preferred embodiments of the present invention have been described, the present invention is not limited to these embodiments. Additions, omissions, substitutions, and other modifications can be made to the present invention without departing from the spirit and scope of the present invention. The present invention is not limited to the above-mentioned description, and is only limited by the scope of the appended claims.

What is claimed is:

1. A guide sheath which is configured to be guided by an internal introduction device and be inserted into a body, and which has a channel through which a medical device is capable of being inserted so as to guide a distal end of the medical device to a target area, the guide sheath comprising:
    an elongated member extending along a longitudinal axis;
    a first conduit line formed on a central axis of the elongated member;
    a pair of second conduit lines formed and disposed radially outside the first conduit line;
    a pair of manipulation wires disposed in the second conduit lines and extending along the longitudinal axis of the elongated member so as to be capable of advancing and retracting; and
    a bent section formed of a thermoplastic resin, the bent section being configured to be bent in accordance with advance or retraction of the manipulation wires, wherein
    the bent section includes portion walls formed at positions which are radially outside both the first conduit line and the second conduit lines and which are between an outer surface of the bent section and the second conduit lines,
    in the portion walls, soft sections having predetermined bending stiffness and hard sections formed to have bending stiffness larger than the soft sections by cross-linking the thermoplastic resin are alternately disposed along the longitudinal axis, and
    distal end sections of the manipulation wires are fixed to the hard sections.

2. The guide sheath according to claim 1, wherein
    the soft sections are formed of a kneading material in which the thermoplastic resin and a cross-linking accelerator are kneaded, and
    the hard sections are formed of a cross-linked material obtained by radiating ionizing radiation to the kneading material to cross-link the thermoplastic resin.

* * * * *